(12) United States Patent
Chien (10) Patent No.: US 8,544,470 B2
(45) Date of Patent: Oct. 1, 2013

(54) REPLACEABLE FOREHEAD LINER

(75) Inventor: Chih Tsan Chien, Tu-Cheng (TW)

(73) Assignee: Apex Medical Corp., Taipei County (TW)

( * ) Notice: Subject to any disclaimer, the term of this patent is extended or adjusted under 35 U.S.C. 154(b) by 342 days.

(21) Appl. No.: 12/950,677

(22) Filed: Nov. 19, 2010

(65) Prior Publication Data
US 2012/0012113 A1    Jan. 19, 2012

(30) Foreign Application Priority Data
Jul. 16, 2010  (TW) .............................. 99123463 A (51) Int. Cl.
*A62B 18/02* (2006.01)
*A62B 9/04* (2006.01)

(52) U.S. Cl.
USPC ................................. 128/206.21; 128/202.27

(58) Field of Classification Search
USPC ............. 128/202.27, 205.25, 206.21, 206.23, 128/206.24, 206.28, 207.11, 207.13
See application file for complete search history.

(56) References Cited

U.S. PATENT DOCUMENTS

| | | | | |
|---|---|---|---|---|
| 7,975,692 B2* | 7/2011 | Eifler et al. | | 128/205.25 |
| 8,171,934 B1* | 5/2012 | Ho | | 128/207.11 |
| 2005/0011522 A1* | 1/2005 | Ho et al. | | 128/206.21 |
| 2007/0221226 A1* | 9/2007 | Hansen et al. | | 128/206.21 |
| 2008/0314390 A1* | 12/2008 | Kwok et al. | | 128/207.11 |
| 2011/0094517 A1* | 4/2011 | Kwok et al. | | 128/206.28 |
| 2011/0162654 A1* | 7/2011 | Carroll et al. | | 128/206.21 |
| 2011/0174311 A1* | 7/2011 | Gunaratnam | | 128/207.11 |
| 2012/0103340 A1* | 5/2012 | Chu et al. | | 128/206.21 |

* cited by examiner

*Primary Examiner* — Kristen Matter
(74) *Attorney, Agent, or Firm* — Muncy, Geissler, Olds & Lowe, PLLC (57) ABSTRACT

A replaceable forehead liner for the continuous positive airway pressure machine, which includes a base, a support, and a locking member. The base has a plurality of flexible pads and a connecting member for bridging the flexible pads. The support has a plurality of support pillars and a support plate connecting the support pillars. The support pillars, the support plate, and the flexible pads form a hollow area, and each support pillar has a hollow hole. The hollow area and holes make the support pillars elastic and compressible. The locking member forms off the surface of the support pillars and the support plate, with the locking member being wider than the side of the hollow area. The locking member has a locking portion for engaging to the clipping portion of the CPAP mask. Functionally, the replaceable forehead liner is more secured and improves pressure relief for the user.

15 Claims, 13 Drawing Sheets

REPLACEABLE FOREHEAD LINER

BACKGROUND OF THE INVENTION

1. Field of the Invention

The instant disclosure relates to a replaceable forehead liner; in particular, a replaceable forehead liner for a face mask of the continuous positive airway pressure (CPAP) machine.

2. Description of the Related Art

The continuous positive airway pressure machine, or CPAP, is primarily used for treating sleep apnea. Sleep apnea is a sleep disorder characterized by the collapsing of soft tissues around the throat area, which can obstruct breathing during sleep. Individuals with sleep apnea experience difficulty in breathing, and may lead to suffocation in severe cases. Using CPAP, the patient wears a mask that is connected to an air pump. The air pump is delivering pressurized air, which keeps the person's airway open for unobstructed breathing.

To maintain pressurized air, the mask is sealed on the face. To reduce skin irritation, a flexible liner is used for the mask.

Figure 1:
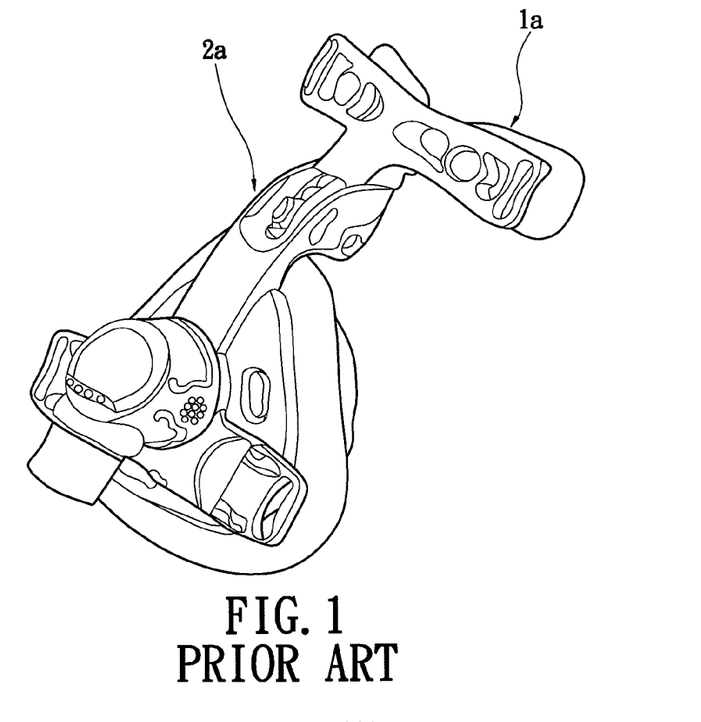
FIG. 1 shows a schematic view of a typical CPAP mask of the prior art.
Figure 2:
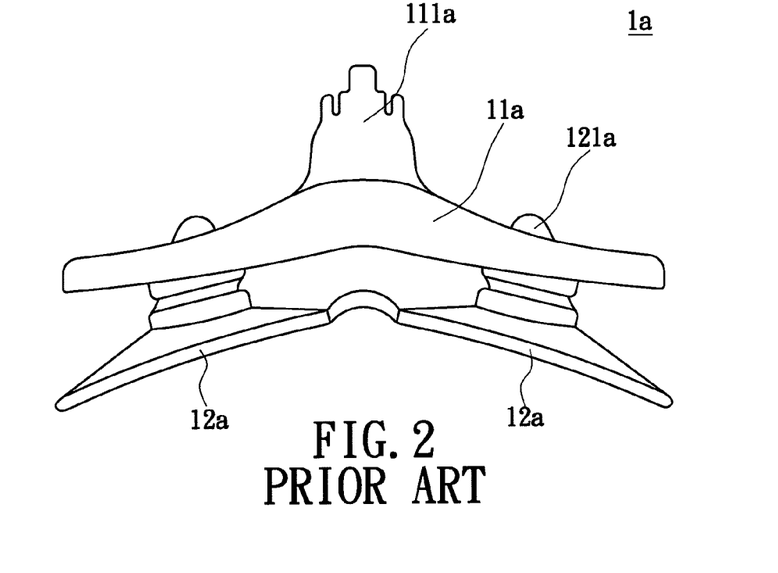
FIG. 2 shows a schematic view of a forehead liner of the CPAP mask in FIG. 1 of the prior art.

As shown in FIGS. 1 and 2, the forehead liner 1a is clipped to the mask 2a. The forehead liner 1a comprises a support arm 11a and two forehead cushions 12a. The forehead cushions 12a clips to the support arm 11a by two quick-clip balls 121a. Similarly, the support arm 11a uses a quick-clip 111a to clip onto the mask 2a. However, the quick-clip features may be insecure; plus, excessive pressure tends to concentrate around the quick-clip regions in causing discomfort to the user.

Figure 3:
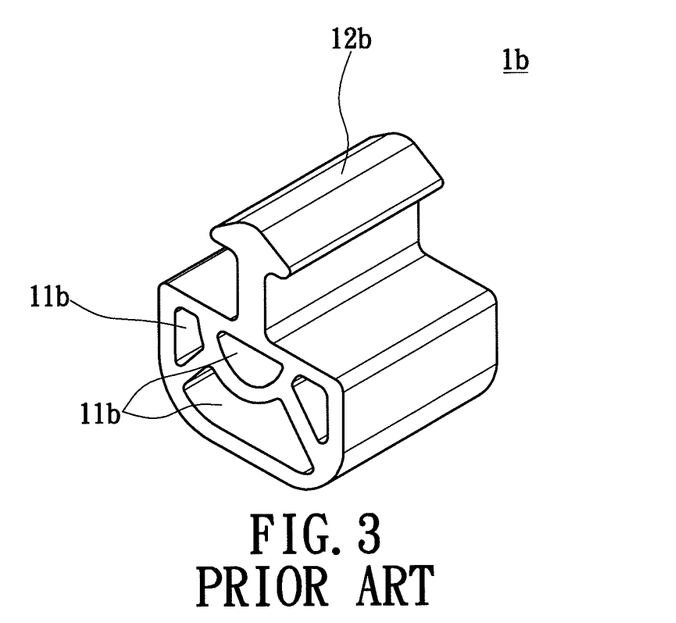
FIG. 3 shows a schematic view of a second typical forehead liner of the CPAP mask of the prior art.

FIG. 3 shows another forehead liner 1b with internal openings 11b in providing flexibility. A T-shaped clipping portion 12b forms off the top of the forehead liner 1b for clipping to the mask 2a (not shown). However, the clipping portion 12b has a small contact area, which can clip insecurely. With the hollow openings 11b, the forehead liner 1b is weaker structurally in relieving the excessive pressure.

Figure 4:
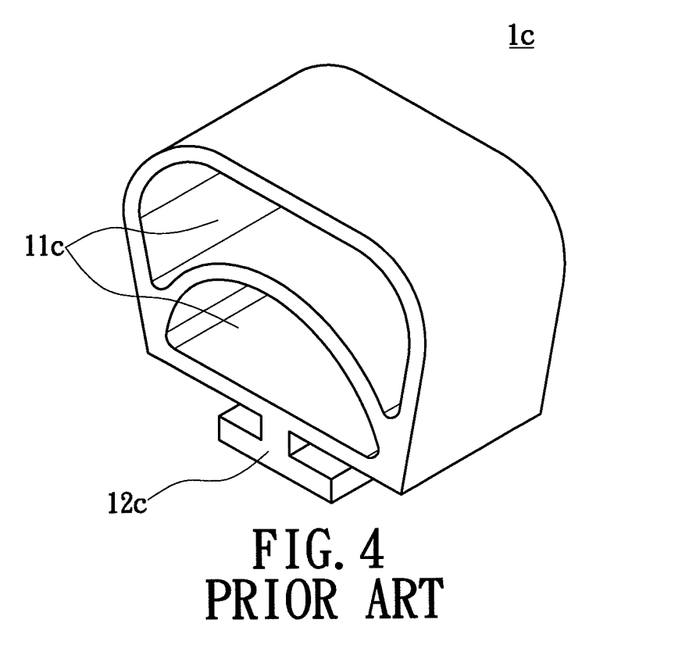
FIG. 4 shows a schematic view of a third typical forehead liner of the CPAP mask of the prior art.

A third typical forehead liner 1c is shown in FIG. 4 with structural similarity to the previous example. Namely, the forehead liner 1c comprises internal openings 11c and a T-shaped clipping portion 12c. Functionally, the forehead liner 1c has similar disadvantages as the forehead liner discussed previously.

Figure 5:
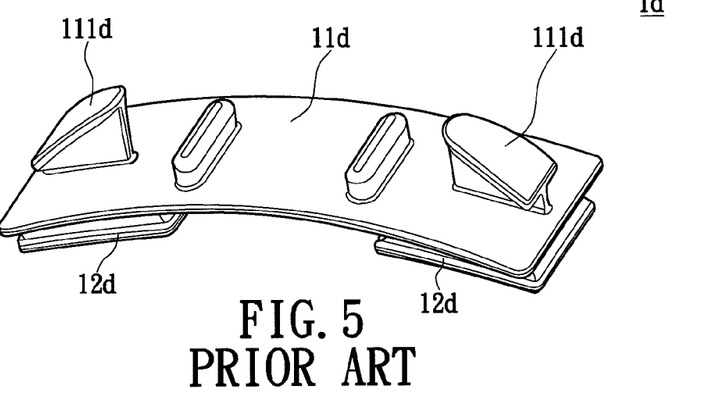
FIG. 5 shows a schematic view of a fourth typical forehead liner of the CPAP mask of the prior art.
Figure 6:
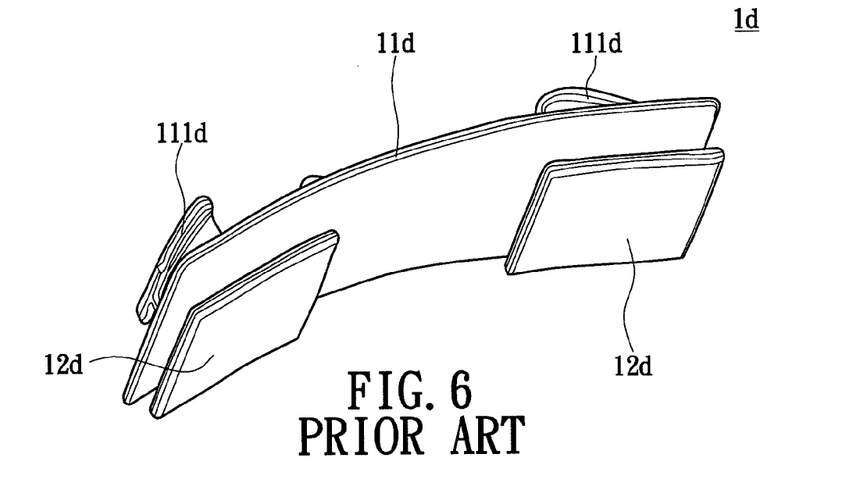
FIG. 6 shows another schematic view of a fourth typical forehead liner of the CPAP mask of the prior art.
Figure 7:
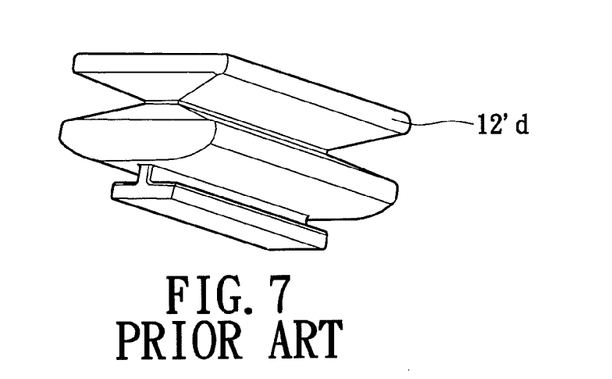
FIG. 7 shows a schematic view of another forehead cushion for a fourth typical forehead liner of the CPAP mask of the prior art.

FIGS. 5 and 6 illustrate a fourth type forehead liner 1d having a support arm 11d with two forehead cushions 12d. Two clipping portions 111d protrude off the top of the support arm 11d for clipping to the mask (not shown). The forehead cushions 12d can be formed integrally with the support arm 11d. Alternatively, as shown in FIG. 7, the forehead cushion 12d' can be a separate piece for clipping to the support arm 11d. However, the slanted clipping portions 111d do not clip easily and are weaker structurally. As a separate unit, the forehead cushion 12d' is less effective in dispersing applied pressure to the user.

To address the above issues, the inventor proposes the following solution.

SUMMARY OF THE INVENTION

The instant disclosure relates to a replaceable forehead liner for the CPAP mask. The advantages include more secured clipping structure to prevent the liner from loosening. Also, the liner is improved structurally to better disperse applied pressure in providing more comfort to the users.

To meet the above object, the instant disclosure provides a replaceable forehead liner for the CPAP mask and a clipping portion of the mask. The liner comprises a base, a support, and at least one locking member.

The base has two flexible pads and a connecting member connecting the flexible pads. Each flexible pad has a inner surface and a outer surface, where the inner surface snugs to the user's forehead. Preferably, each inner surface has at least one embedded groove.

The support member has two support pillars extending from the outer surface of the two flexible pads, and also includes a support plate integrally joining the support pillars. The support member and the base member define a hollow area therebetween. Furthermore, each support pillar forms a hollow hole, which makes the support pillar elastic and compressible. The locking member forms off the surface of the support pillars and the support plate, and the locking member is wider than the side of the hollow area. The locking member has a locking portion for clipping to the clipping portion of the mask.

The instant disclosure has the following advantages. Structurally, the hollow area and holes enable better pressure relief. Also, the flexible pads can be adjusted slightly to reduce the occurrence of pressure sores, thus providing better comfort to the users. The locking member is wider than the hollow area and the hollow holes, which offers more contact area for engaging the liner to the mask more securely. In addition, the grooves on the flexible pads provide friction to prevent the liner from slipping off the forehead.

In order to further appreciate the characteristics and technical contents of the instant disclosure, references are hereunder made to the detailed descriptions and appended drawings in connection with the instant disclosure. However, the appended drawings are merely shown for exemplary purposes, rather than being used to restrict the scope of the instant disclosure.

DETAILED DESCRIPTIONS OF THE PREFERRED EMBODIMENTS

Figure 8:
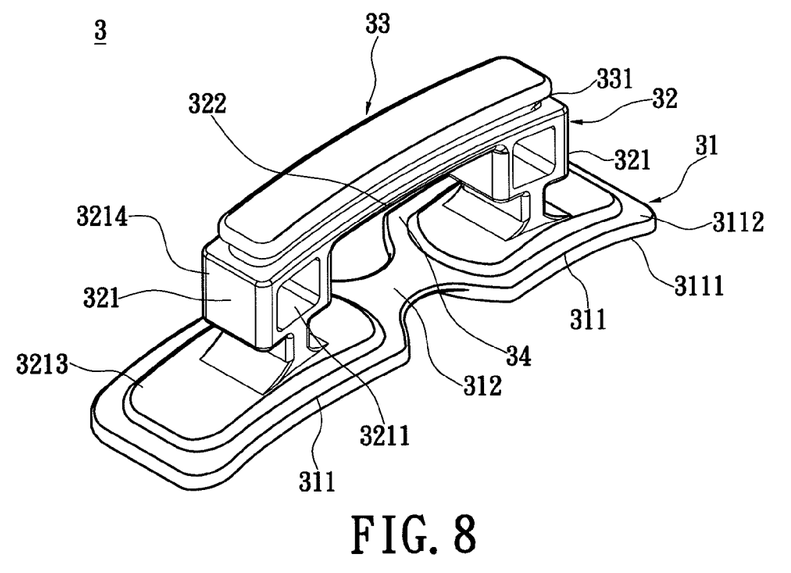
FIG. 8 shows a schematic view of a replaceable liner for the first embodiment.
Figure 9:
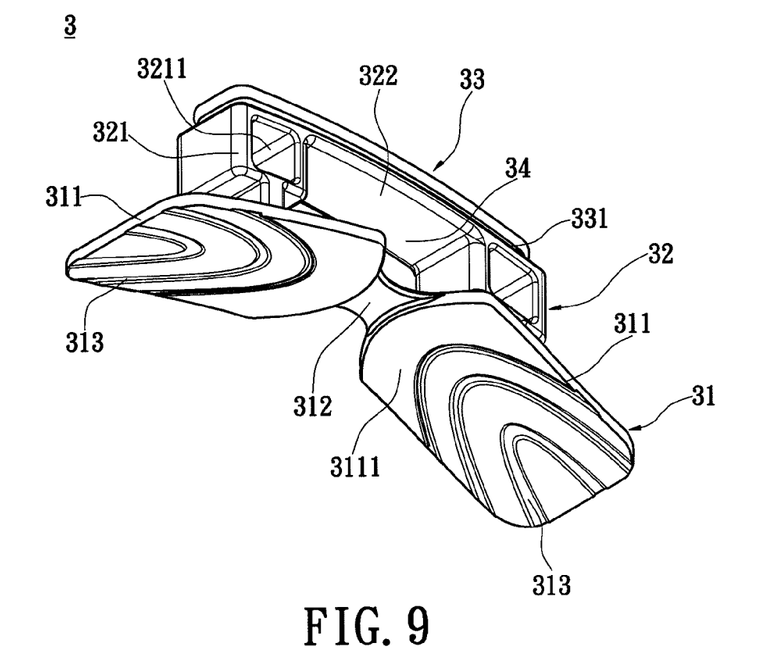
FIG. 9 shows another schematic view of a replaceable liner for the first embodiment
Figure 10:
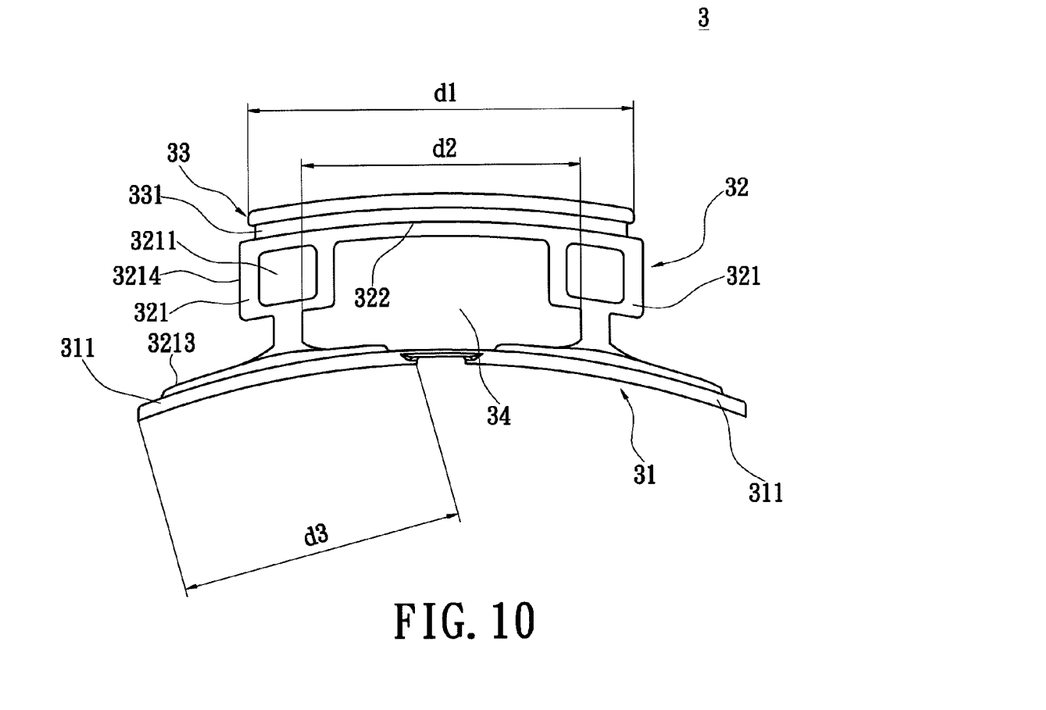
FIG. 10 shows a plan view of a replaceable liner for the first embodiment.

FIGS. 8 to 10 show the replaceable forehead liner 3 according to the first embodiment of the instant disclosure. The replaceable forehead liner 3 is formed integrally comprising a base 31, a support 32, and a locking member 33. The base 31 has two flexible pads 311 and a connecting member 312 for bridging the flexible pads 311 as one integral body. The flexible pad 311 is elastic and compressible with an inner surface 3111 on the face side and an outer surface 3112 on the flip side. Preferably, the inner surface 3111 of each flexible pad 311 has at least one groove 313. The groove 313 provides friction in preventing the liner from slipping off the face and also diverts perspirations. Structurally, the flexible pads 311 can be either angled or leveled horizontally.

The support 32 has two support pillars 321 and a support plate 322. Each support pillar 321 is formed off the outer surface 3112 of the flexible pad 311. The support plate 322 extends from the ends of the support pillars 321 in bridging the support pillars 321 as one integral body. Also, the support pillars 321, the support plate 322, and the flexible pads 311 together define a hollow area 34. Furthermore, each support pillar 321 further has a hollow hole 3211 for providing better elasticity and flexibility. Each support pillar 321 has a supporting base 3213 elevated off the outer surface 3112 of the flexible pad 311, and including a supporting arm 3214 extending off the supporting base 3213. The supporting arm 3214 holds the hollow hole 3211.

The locking member 33 forms off the support pillars 321 and the support plate 322. For increasing the clipping area, as shown in FIG. 10, a length d1 of the locking member 33 must be greater than or equal to a length d2 of the hollow area 34. The locking member 33 comprises a grooved locking portion 331. Preferably, the length d3 of each flexible pad 311 is greater than or equal to the length d2 of the hollow area 34, for increasing the contact surface to disperse the exerted pressure.

Figure 11:
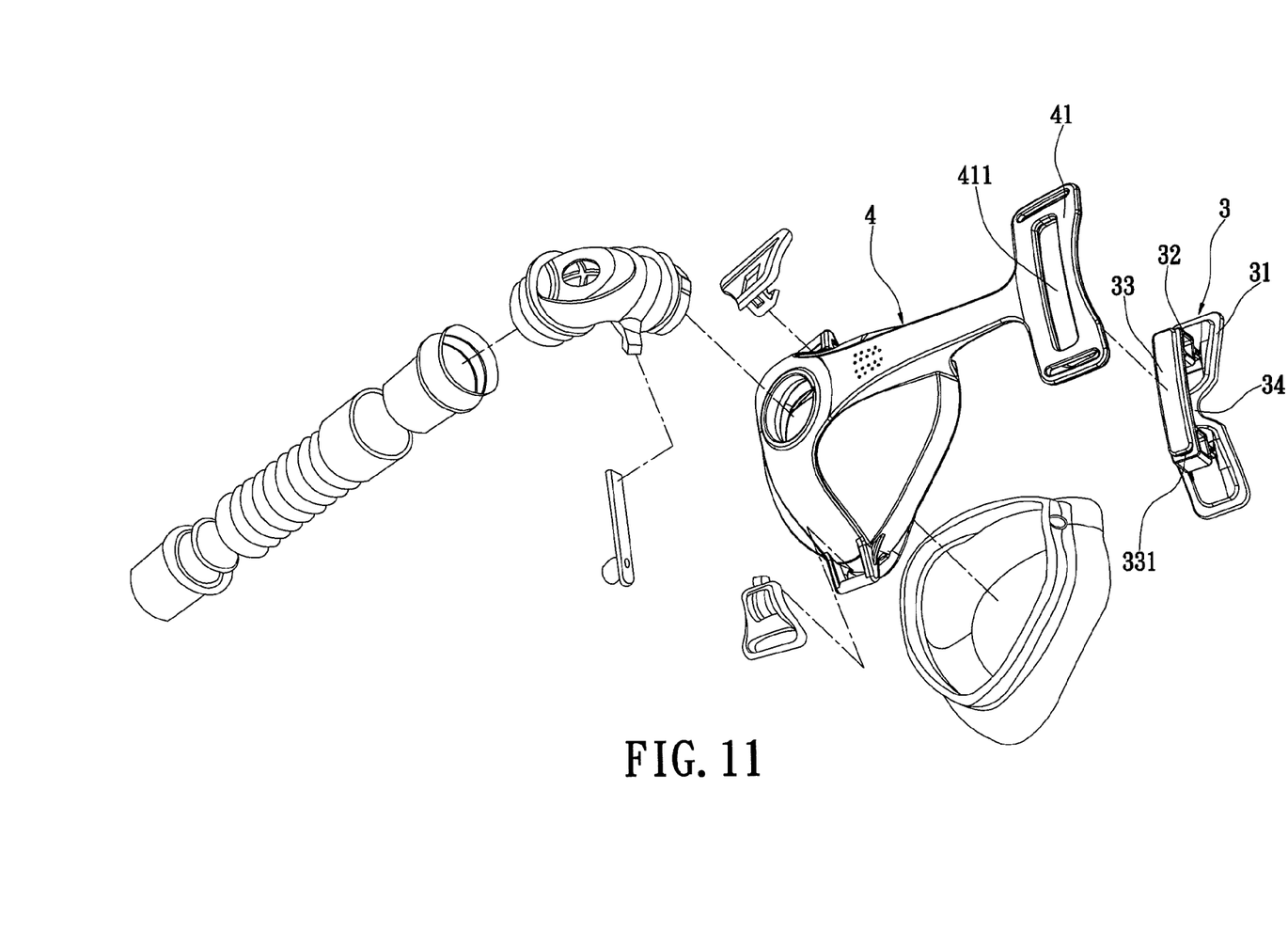
FIG. 11 shows an assembly view of a CPAP mask.

As shown in FIG. 11, the replaceable forehead liner 3 can be clipped onto a CPAP mask 4. Structurally, the mask 4 has a clipping portion 41 for engaging the locking portion 331 of the locking member 33.

Figure 12:
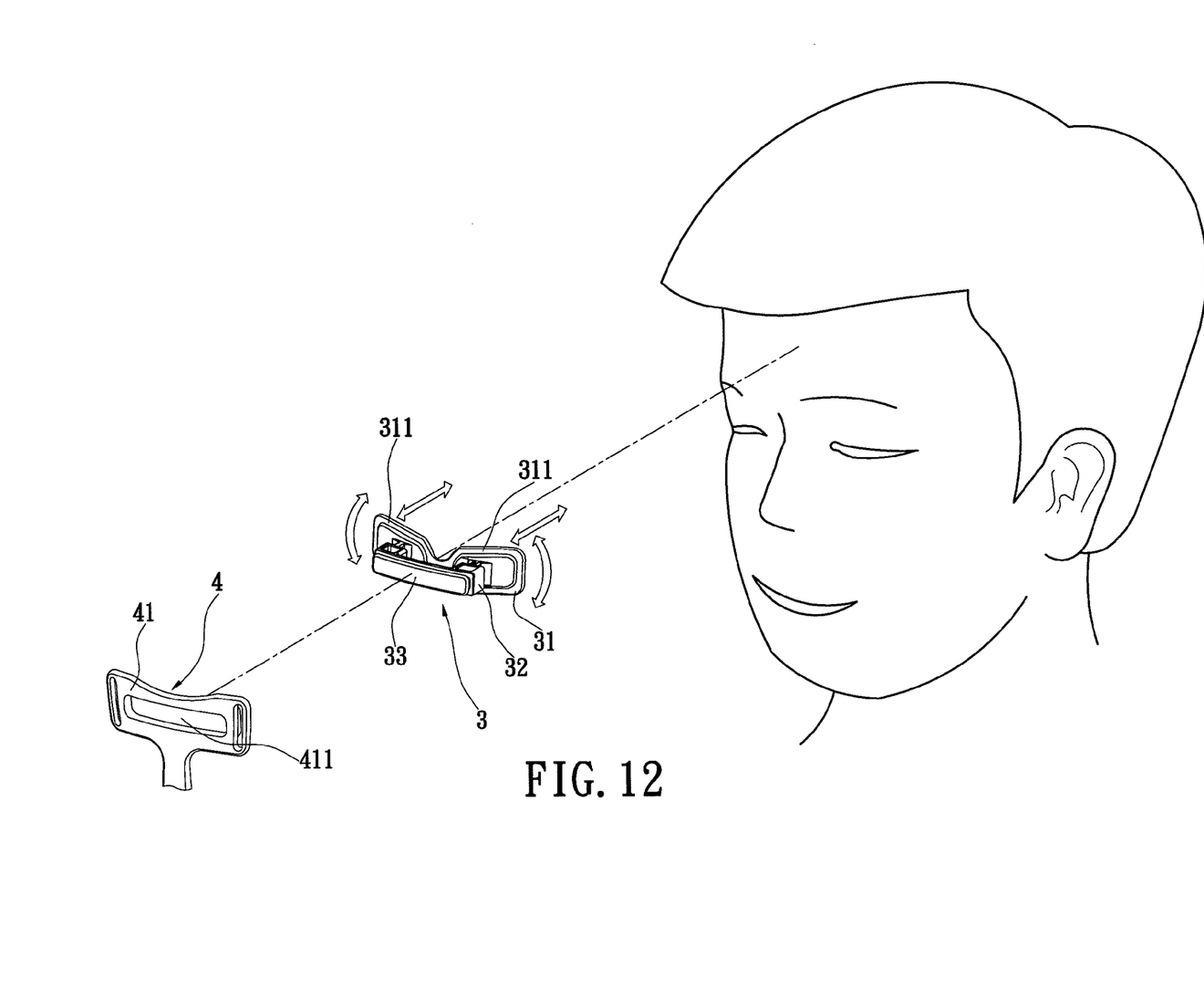
FIG. 12 shows a schematic view of using a replaceable liner.

FIG. 12 shows a schematic view of using the replaceable forehead liner 3. Also refer to FIGS. 8 and 9. The flexible pads 311 and the connecting member 312 can be slightly adjusted to fit the user's forehead for comfort. Furthermore, the hollow area 34 and the hollow holes 3211 of the support pillars 321 allows flexibility for the support pillars 321 and the support plate 322 for providing better comfort to the users. On the other hand, the grooves 313 on the inner surface 3111 of the flexible pad 311 prevent the liner from slipping off the forehead. The grooves 313 also help to divert perspirations in providing more comfort to the users.

In the instant embodiment, the clipping portion 41 has an engaging slot 411 for engaging to the locking portion 331.

Since the locking member 33 is wider than the hollow area 34, the locking portion 331 is wider accordingly, which provides more secured engagement to the mask 4.

Figure 13:
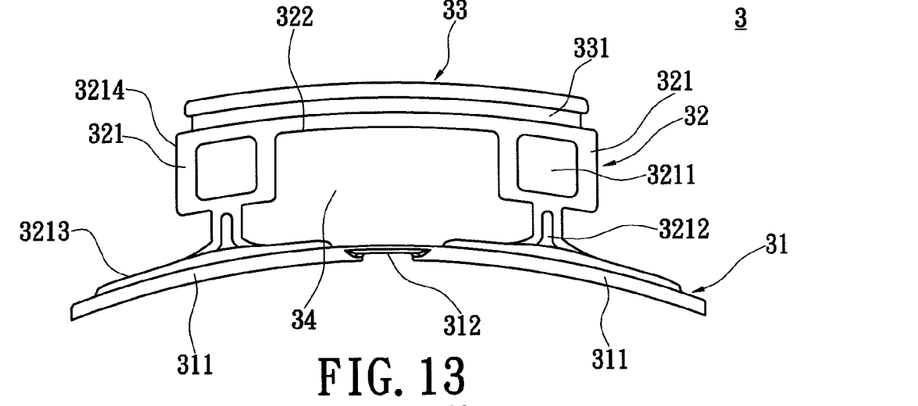
FIG. 13 shows a first plan view of a replaceable liner of the first embodiment.

Furthermore, the instant embodiment can be modified as shown in FIG. 13. Each support pillar 321 of the support 32 forms an opening 3212. The opening 3212 is smaller than the hollow holes 3211, and the opening 3212 is formed on the supporting arm 3214 near the flexible pad 311. The openings 3212 provide additional flexibility to the supporting arms 3214 of the support pillars 321 for dispersing exerted pressure.

Figure 14:
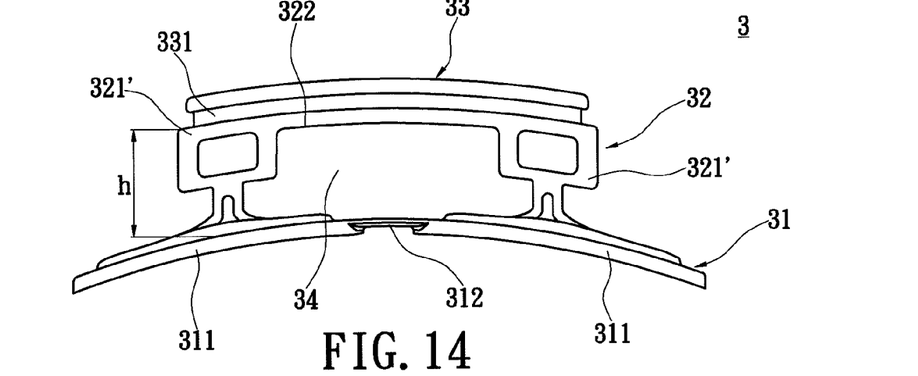
FIG. 14 shows a second plan view of a replaceable liner of the first embodiment.

As shown in FIG. 14 of the instant embodiment, the height h of the support pillars 321' of the support 32 is shorter than 321. Based on the preference of the user, the replaceable forehead liner 3 with appropriate height h can be selected.

Figure 15:
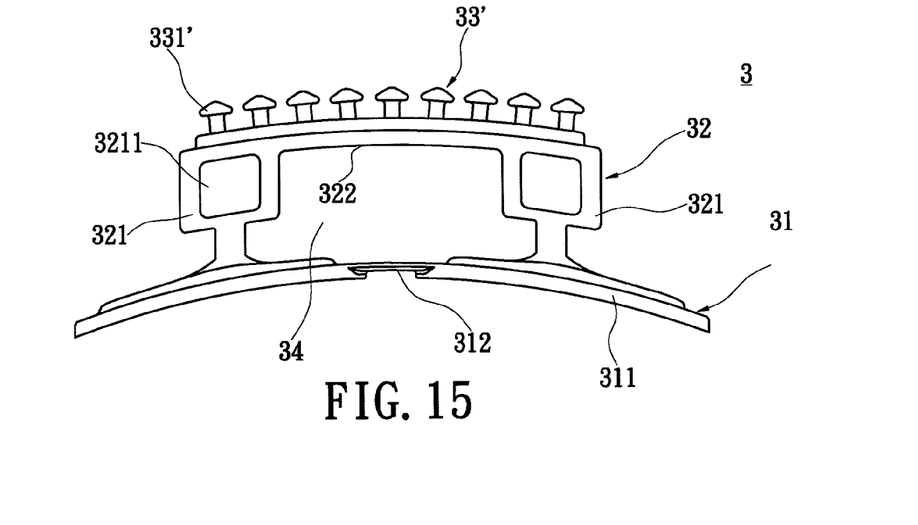
FIG. 15 shows a third plan view of a replaceable liner of the first embodiment.
Figure 16:
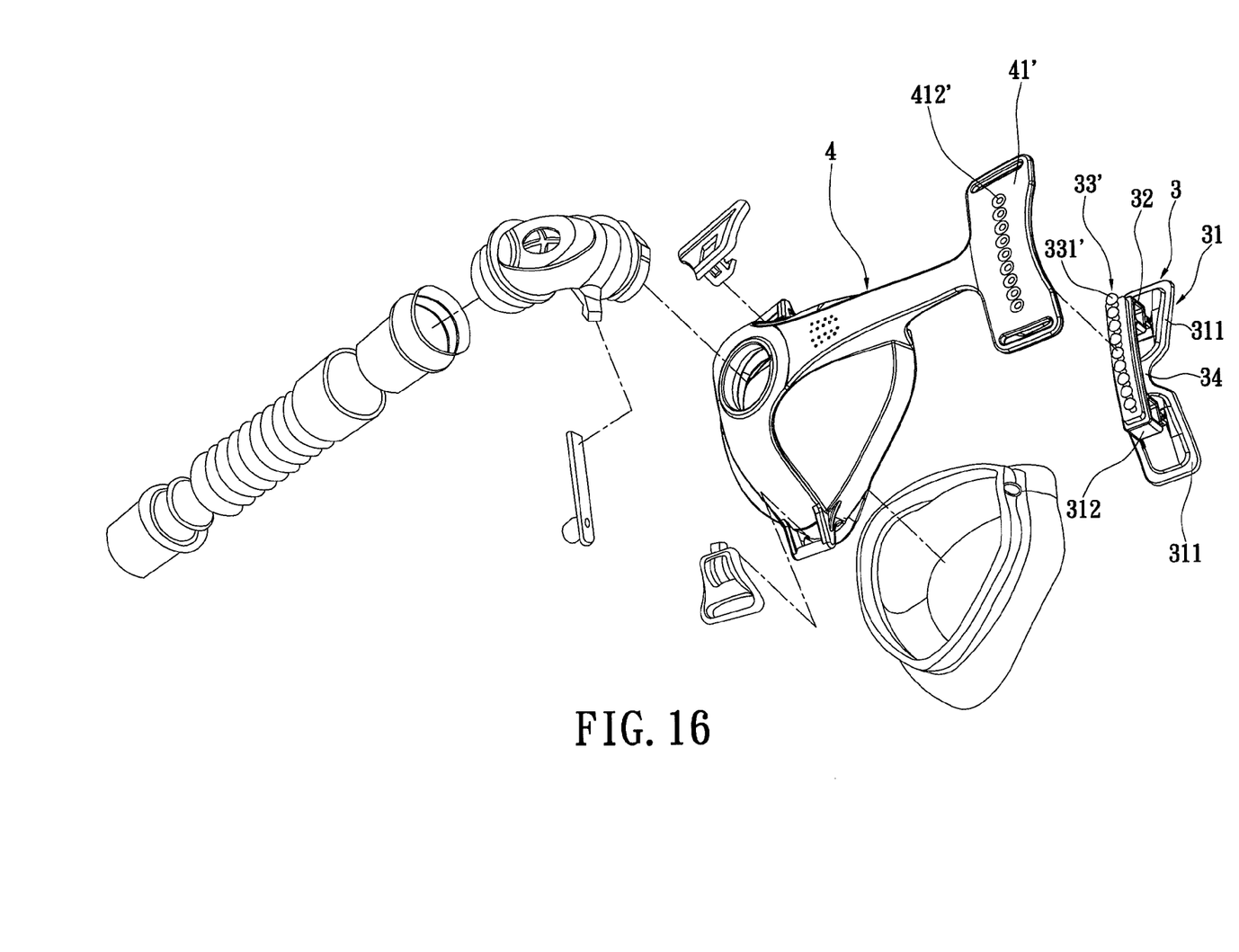
FIG. 16 shows another assembly view of a CPAP mask.

Alternatively, FIGS. 15 and 16 show another variation of the instant embodiment. Namely, the locking portion 331' of the locking member 33' can be a plurality of spaced male engaging members. Accordingly, the clipping portion 41' of the mask 4 has a plurality of female engaging slots 412' for interlocking to the male engaging members of the locking portion 331'. Such interlocking alternative also disperses applied pressure in preventing the occurrence of pressure sores to the users.

Figure 17:
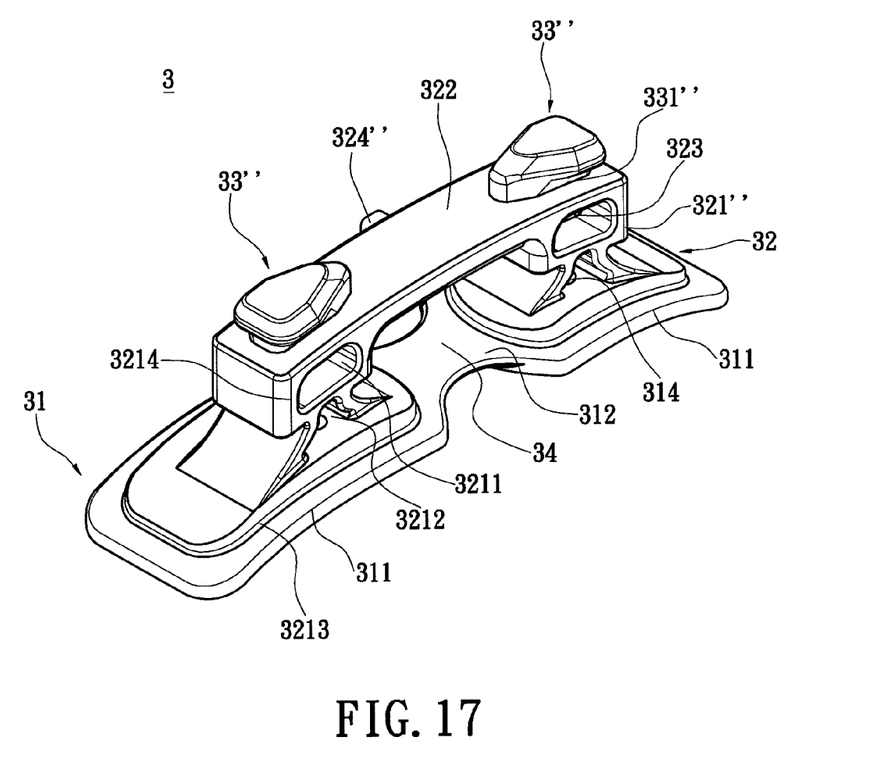
FIG. 17 shows a schematic view of a replaceable liner of the second embodiment.
Figure 18:
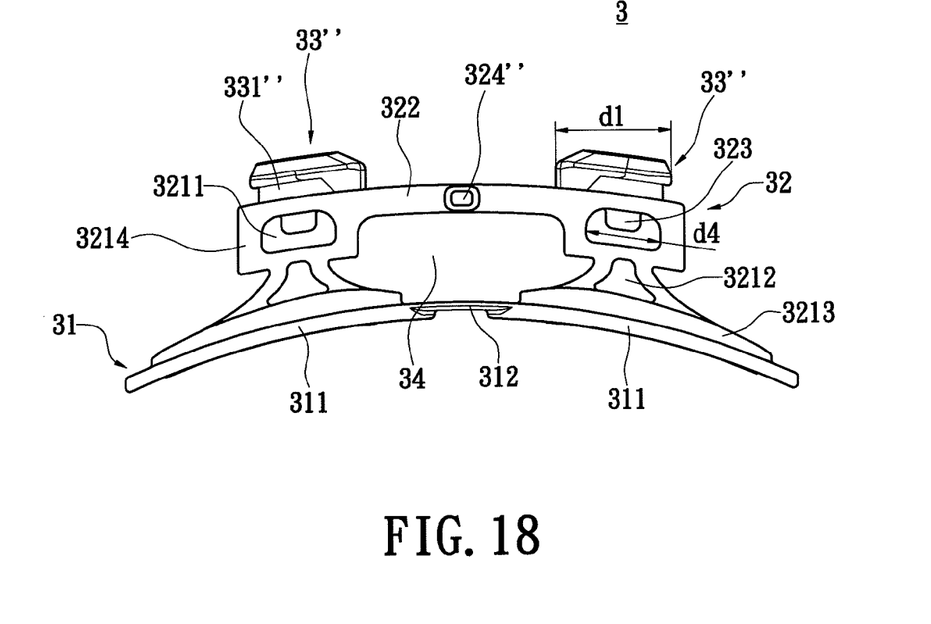
FIG. 18 shows a plan view of a replaceable liner of the second embodiment.

FIGS. 17 and 18 show a second embodiment of the instant disclosure. The second embodiment has two locking members 33" formed off the support pillars 321". The length d1 of the locking member 33" is greater than or equal to the length d4 of the hollow hole 3211 for providing greater clipping area. The locking portion 331" is formed as a groove around the outer surface of the locking member 33". Accordingly, the clipping portion of the mask has corresponding engaging slots (not shown).

Figure 19:
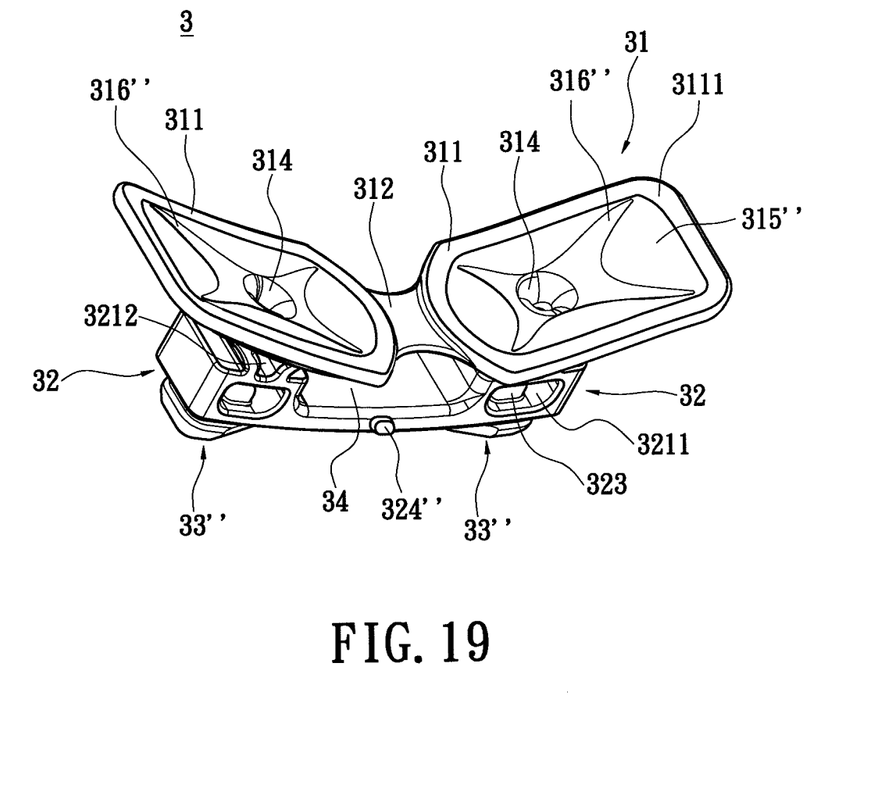
FIG. 19 shows another schematic view of a replaceable liner of the second embodiment.

The support 32 can further have two cushions 323. Each cushion 323 is formed inside the hollow hole 3211 pointing towards the base 31. When the support 32 is under pressure and thus deforms, the cushions 323 butt against the other side of the hollow hole 3211 in minimizing the deformation of the support 32. In turn, the cushions 323 act to maintain the structural integrity of the liner relative to the mask. As shown in FIGS. 17 and 19, the base 31 can further have two thru holes 314. Each thru hole 314 is formed inside the flexible pad 311, with an internal passage thru the supporting base 3213 of the support 32 to the opening 3212. In turn, the thru holes 314 act as air vents, such as venting heat away from the user in providing greater comfort.

In addition to the thru holes 314, the inner surface 3111 of the flexible pad 311 can further have a concave portion 315" and a protrusion portion 316". The thru hole 314, the concave portion 315", and the protrusion portion 316" keeps the flexible pad 311 from sticking uncomfortably to the forehead of the user.

Figure 20:
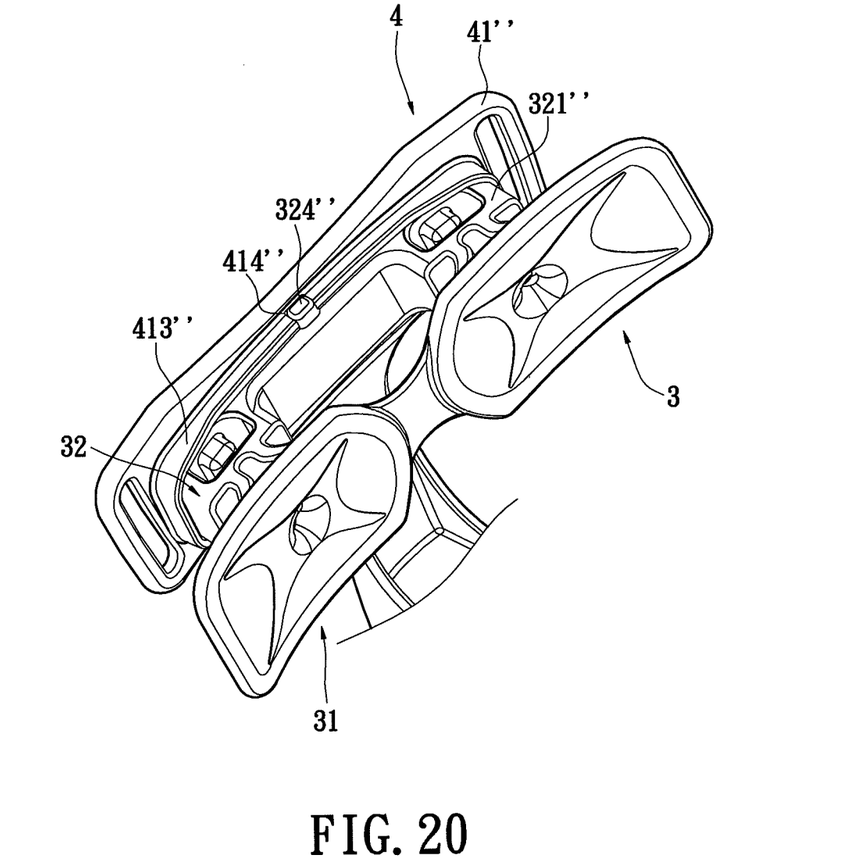
FIG. 20 shows an assembly view of a CPAP mask of the second embodiment.

Furthermore, as shown in FIGS. 17 to 19, a set piece 324" can be disposed on the outer edge of the support plate 322 of the support 32. When attaching the replaceable forehead liner 3 to the mask 4, the set piece 324" acts as a reference point. As shown in FIG. 20, a lip 413" is formed about the clipping portion 41" corresponding to the outer edge of the support 32. At the corresponding location to the set piece 324", a set groove 414" is formed on the lip 413". When assembling the replaceable forehead liner 3 to the mask 4, the set groove 414" receives the set piece 324", and the support 32 is partially enclosed behind the lip 413". The area where the lip 413" covers the support pillar 321" should be relatively higher to ensure a secured assembly. Noteworthy, the cushions 323, thru holes 314, the concave portion 315", the protrusion portion 316, and the set piece 324" of the instant embodiment can also be applied to the liner in the first embodiment (not shown graphically).

In summary, the instant disclosure utilizes the hollow area and hollow holes to improve the pressure distribution of the liner. The flexible pads can be adjusted slightly for providing better comfort, and the contacting area is increased to relieve the pressure more proportionally. Furthermore, the locking member is wider than the side of the hollow area or the hollow hole, which increase the locking area for more secured attachment. The grooves on the flexible pads reduce the likeliness of the liner slipping off accidentally and help diverts off perspirations.

The descriptions illustrated supra set forth simply the preferred embodiments of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. A replaceable forehead liner for a CPAP mask having a clipping portion, comprising:
    a forehead contact member having a pair of flexible pads integrally joined by a connecting bridge member, each pad defining an inner contact face and an outer frontal face;
    a support member comprising a pair of support pillars, the support pillars respectively and frontally extending from the outer frontal faces of the flexible pads, wherein each support pillar includes a narrower root portion having an opening arranged thereon and a wider head portion having a hollow hole arranged thereon,
    wherein an extending direction of the openings and the hollow holes are substantially parallel,
    wherein the extending direction of the openings and the hollow holes are substantially normal to the frontally extending direction of the support pillars;
    a support plate integrally joining the support pillars, wherein the forehead contact member and the support member define a hollow portion therebetween, thereby forming an elastic and flexible support structure; and
    a locking member extending from the support member having a length greater than a length of the hollow portion and having a locking portion for engaging to the clipping portion of the mask.

2. The replaceable forehead liner for the CPAP mask of claim 1, wherein each flexible pad has at least one groove on the inner contact face.

3. The replaceable forehead liner for the CPAP mask of claim 1, wherein each opening is smaller than each hollow hole; wherein the openings are respectively located near the flexible pads.

4. The replaceable forehead liner for the CPAP mask of claim 3, wherein each wider head portion further includes a cushion arranged in the hollow hole protruding toward the inner contact face of the wider head portion.

5. The replaceable forehead liner for the CPAP mask of claim 4, wherein each flexible pad of the forehead contact member has a thru hole; wherein the thru holes are respectively and internally connected to the openings of the support member.

6. The replaceable forehead liner for the CPAP mask of claim 5, wherein the inner contact face of each flexible pad forms a concave portion connected to the thru hole; wherein the wall of the concave portion forms a protrusion portion.

7. The replaceable forehead liner for the CPAP mask of claim 1, wherein the locking portion of the locking member has a groove-like shape; wherein the clipping portion of the mask has an engaging slot for the locking portion.

8. A replaceable forehead liner for a CPAP mask, wherein the mask has a clipping portion, comprising:
    a forehead contact member having a pair of flexible pads connected by a connecting bridge member, each flexible pad defining an inner contact face and an outer frontal face;
    a support member comprising a pair of support pillars respectively and frontally extending from the outer frontal faces of the flexible pads, wherein each support pillar includes a narrower root portion having an opening arranged thereon and a wider head portion having a hollow hole arranged thereon,
    wherein an extending direction of the openings and the hollow holes are substantially parallel,
    wherein the extending direction of the openings and the hollow holes are substantially normal to the frontally extending direction of the support pillars;
    a support plate integrally joining the support pillars, wherein the support member and the forehead contact member define a hollow portion therebetween, thereby forming an elastic and flexible support structure; and
    a pair of locking members extending from a surface of the support pillars, each locking member having a length greater than a length of the hollow hole and having a locking portion for engaging to the clipping portion of the mask.

9. The replaceable forehead liner for the CPAP mask of claim 8, wherein each flexible pad has at least one groove on the inner contact face.

10. The replaceable forehead liner for the CPAP mask of claim 8, wherein each opening is smaller than each hollow hole; wherein the openings are respectively located near the flexible pads.

11. The replaceable forehead liner for the CPAP mask of claim 10, wherein each wider head portion further includes a cushion arranged in the hollow hole protruding toward the inner contact face of the wider head portion.

12. The replaceable forehead liner for the CPAP mask of claim 11, wherein each flexible pad of the forehead contact member has a thru hole; wherein the thru holes are respectively and internally connected to the openings of the support member.

13. The replaceable forehead liner for the CPAP mask of claim 12, wherein the inner contact face of each flexible pad forms a concave portion connected to the thru hole; wherein the wall of the concave portion forms a protrusion portion.

14. The replaceable forehead liner for the CPAP mask of claim 8, wherein the locking portion of the locking member has a groove-like shape; wherein the clipping portion of the mask has an engaging slot for the locking portion.

15. The replaceable forehead liner for the CPAP mask of claim 14, wherein the clipping portion has a lip formed thereon corresponding to an outer edge of the support member; wherein the support plate of the support member has a set piece; wherein the lip has a set groove formed thereon corresponding to the location of the set piece; wherein the set piece engages the set groove; wherein the support member is partially covered by the lip.

* * * * *